United States Patent [19]
Allen

[11] Patent Number: 5,226,814
[45] Date of Patent: Jul. 13, 1993

[54] ORTHODONIC BRACKET

[76] Inventor: Michael D. Allen, 606 Wildgrove, Garland, Tex. 75041

[21] Appl. No.: 880,132

[22] Filed: May 7, 1992

[51] Int. Cl.$^5$ .............................................. A61C 3/00
[52] U.S. Cl. ............................................. 433/15; 433/8
[58] Field of Search ............... 433/8, 9, 10, 11, 12, 433/13, 14, 15, 16, 17, 18, 19, 20, 21, 22, 23, 24

[56]  References Cited
U.S. PATENT DOCUMENTS

| | | | |
|---|---|---|---|
| 1,991,047 | 2/1935 | Boyd et al. | 433/11 |
| 2,236,042 | 3/1941 | Terwilliger | 433/14 |
| 2,527,526 | 10/1950 | Brusse | 433/15 |
| 2,854,747 | 10/1958 | Lewis | 433/8 |
| 2,958,945 | 11/1960 | Waldman | 433/15 |
| 2,971,258 | 2/1961 | Bien | 433/17 |
| 3,110,105 | 11/1963 | Berman et al. | 433/14 |
| 3,164,901 | 1/1965 | Wallshein | 433/16 |
| 3,218,715 | 11/1965 | Wallshein | 433/15 |
| 3,292,260 | 12/1966 | Jenkins | 433/15 |
| 3,307,261 | 3/1967 | Steiner | 433/15 |
| 3,374,542 | 3/1968 | Moylan | 433/8 |
| 3,414,976 | 12/1968 | Steiner | 433/15 |
| 3,461,558 | 8/1969 | Miller et al. | 433/15 |
| 3,477,128 | 11/1969 | Andrews | 433/16 |
| 3,504,438 | 4/1990 | Wittman et al. | 433/8 |
| 3,626,593 | 12/1971 | Ridgeway | 433/11 |
| 3,765,091 | 10/1973 | Northcutt | 433/9 |
| 4,227,876 | 10/1980 | Fogel et al. | 433/11 |
| 4,416,627 | 11/1983 | Beazley | 433/18 |
| 4,531,911 | 7/1985 | Creekmore | 433/8 |
| 4,536,154 | 9/1985 | Garton, Jr. et al. | 433/8 |
| 4,551,094 | 11/1985 | Kesling | 433/8 |
| 4,575,337 | 3/1986 | Fujita | 433/8 |
| 4,659,309 | 4/1987 | Merkel | 433/9 |
| 4,799,882 | 1/1989 | Kesling | 433/8 |
| 4,838,786 | 6/1989 | Reher et al. | 433/9 |
| 4,838,787 | 6/1989 | Lerner | 433/14 |
| 4,842,512 | 6/1989 | Kesling | 433/8 |
| 4,877,398 | 10/1989 | Kesling | 433/8 |
| 4,917,602 | 4/1990 | Broussard | 433/8 |
| 4,927,360 | 5/1990 | Pospisil | 433/8 |
| 4,941,825 | 7/1990 | Lerner | 433/14 |
| 5,037,297 | 8/1991 | Lerner | 433/14 |

OTHER PUBLICATIONS

Unitek Corporation flyer illustrating the "Unitwin", bracket.
Unitek Product Catalog illustrating the "Glance" bracket.
ORMCO Product Catalog 1983 (pp. V-11, 20, 21, 23).
Unitek Product Catalog 1978 (pp. 31-33).
Mechanical Principles in Orthodontic Force Control (pp. 246-269, 296-311).

Primary Examiner—John J. Wilson
Attorney, Agent, or Firm—Kenyon & Kenyon

[57]  ABSTRACT

An orthodontic bracket is provided for use with an arch wire to apply corrective forces on a tooth. The orthodontic bracket includes a pair of spaced apart, generally vertically oriented tie-wings for attachment of a force transmitting member or a fastening member to either or both of the tie-wings. Each of the tie-wings includes a slot therein for receiving the arch wire. The orthodontic bracket also includes a pair of extension members engageable with the arch wire to control rotation of the tooth. One of the extension members projects mesially from the bracket and the other extension member projects distally from the bracket.

21 Claims, 4 Drawing Sheets

ORTHODONIC BRACKET

FIELD OF THE INVENTION

This invention relates generally to orthodontic devices and, more particularly, to orthodontic brackets used in corrective orthodontic treatment.

BACKGROUND INFORMATION

Orthodontic brackets are used with arch wires and elastomeric chains or other force transmitting members to apply corrective forces on misaligned teeth. The brackets, which are mounted on the teeth, typically include an underlying base portion, which abuts the tooth surface, and an outer portion. The outer portion includes a slot for receiving the arch wire and wing members to facilitate attachment of elastomeric chains or ligatures. Brackets may also include hook members for attachment of additional force transmitting devices.

Conventional brackets generally known as "single wing" brackets have an outer portion comprising a single vertically-oriented bar with a slot forward therein for receiving the arch wire. Single wing brackets may also include a pair of horizontal extension members for rotation control during tooth movement.

Conventional brackets generally known as twin-MDA brackets have an outer portion comprising a pair of parallel, vertically-oriented bars with a slot formed in each bar to receive the arch wire.

Many conventional brackets fail to provide adequate rotation control during tooth movement or true vertical force transmission between brackets mounted on upper and lower teeth. As a result, use of these brackets may cause the creation of gaps between teeth like, for example, gaps at the cuspid bicuspid incisal interface. These gaps are aesthetically undesirable and may affect long term dental health.

Accordingly, one object of this invention is to provide brackets having improved rotation control during tooth movement.

Another object of this invention is to provide brackets that when placed on upper and lower teeth enable generally true vertical force transmission between the upper and lower teeth.

SUMMARY OF THE INVENTION

The present invention is directed to an orthodontic bracket for use with an arch wire to apply corrective forces on a tooth. The orthodontic bracket includes a pair of spaced-apart, generally vertically oriented tie-wings for attachment of a force transmitting member or a fastening member to either or both of the tie-wings. Each of the tie-wings includes a slot therein for receiving the arch wire. The bracket also includes a pair of extension members that are engagable with the arch wire to control rotation of the tooth. One of the extension members projects mesially from the bracket and the other extension member projects distally from the bracket.

According to one embodiment of the invention, the bracket is provided with a hook member extending gingivally from one of the tie-wings. The hook member enables attachment of a spring or other force transmitting device to the bracket.

One advantage of brackets constructed in accordance with the present invention is that they allow improved rotation control during tooth movement. The horizontally projecting extension members engage the arch wire to inhibit rotation. When used on cuspids, for example, the extension members inhibit disto-lingual rotation during retraction and mesio-lingual rotation during protraction.

The extension members are adjustable, enabling a practitioner to vary the degree of rotation control provided.

Rotation control is further enhanced by the twin tie-wing design of the bracket, which allows an elastic chain to be tied to either of the two tie-wings. In this manner, force can be applied to one side of the tooth's labial surface for tooth movement with reduced rotation.

The twin tie-wing design also provides added versatility of the bracket. When the bracket is used on a cuspid, for example, the twin tie-wing structure allows ligation of maxillary six anteriors to only the mesial tie-wing, leaving the distal tie-wing free for elastic chain attachment for protraction of bicuspids and subsequent posterior teeth.

Another advantage of brackets in accordance with the present invention is that they allow generally true vertical force elastics between brackets on upper and lower teeth. The twin tie-wing structure enables hooks to be positioned on either of the tie-wings. The hooks can thus be positioned on brackets for upper and lower teeth so that they are generally vertically aligned.

BRIEF DESCRIPTION OF THE DRAWINGS

The foregoing and additional objects and advantages of the invention will become more apparent in view of the following detailed description and drawings, in which like reference characters denote like parts.

DETAILED DESCRIPTION

Figure 1:
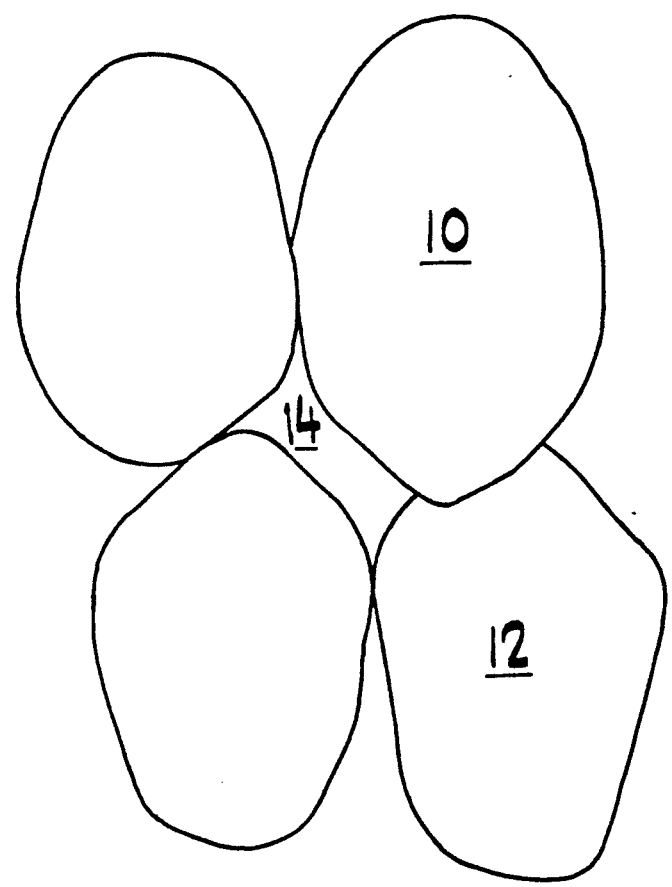
FIG. 1 is an illustration of cuspid malocclusion that may result from use of some conventional brackets.

Use of some conventional brackets in orthodontic treatment may cause undesirable gaps to be created between teeth. FIG. 1 illustrates an example of such malocclusion between a maxillary cuspid 10 and a mandibular cuspid 12. As the figure shows, the maxillary cuspid 10 is excessively mesial relative to the mandibular cuspid 12, creating a gap 14 at the cuspid bicuspid incisal interface. This condition is aesthetically undesirable and may affect long term dental health. The gaps may be caused by the inability of conventional brackets to provide proper rotational control or true vertical force elastics between upper and lower teeth.

Figure 2:
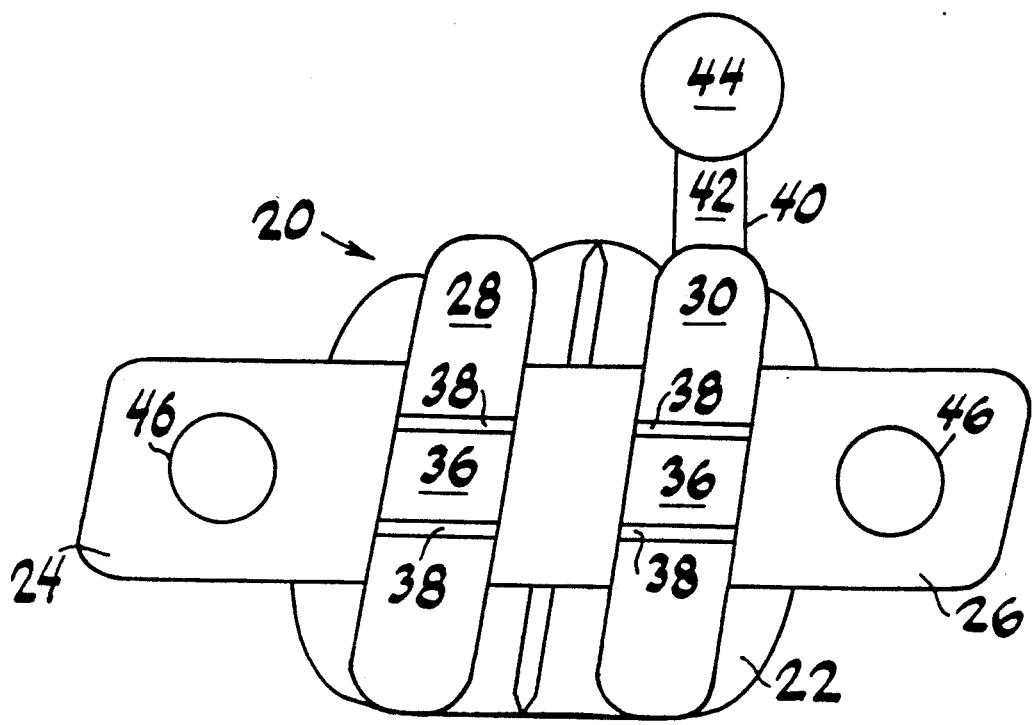
FIG. 2 is a front view of a bracket constructed in accordance with the present invention.
Figure 4:
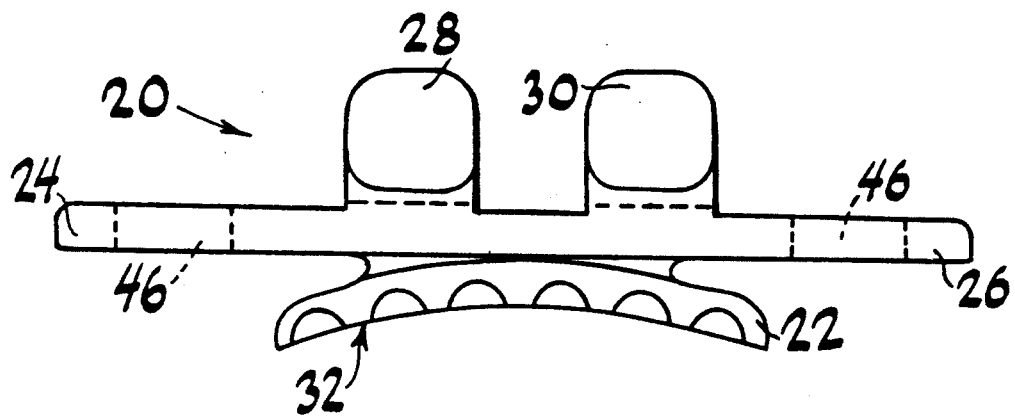
FIG. 4 is a bottom view of the bracket shown in FIGS. 1 and 2.
Figure 3:
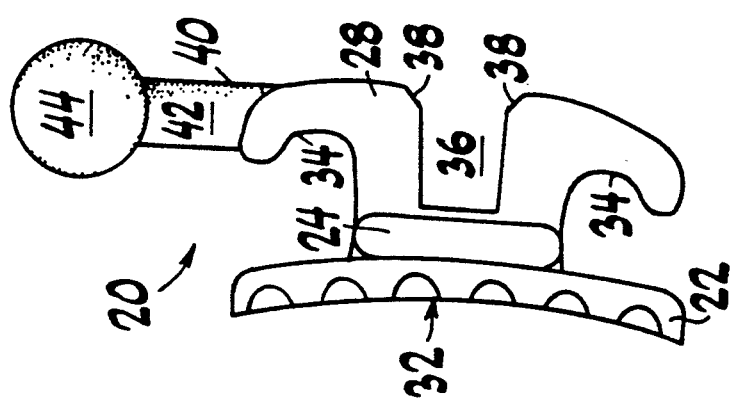
FIG. 3 is a side view of the bracket shown in FIG. 2.

FIGS. 2, 3 and 4 illustrate the front, side and bottom views, respectively, of an orthodontic bracket generally indicated by reference character 20 in accordance with the present invention. The bracket 20 generally comprises an underlying base portion 22, distal and mesial extension members 24 and 26, and distal and mesial tie-wings 28 and 30.

As shown in FIGS. 3 and 4, the base portion 22 includes a tooth abutting surface 32, which is generally contoured to fit the outer shape of a tooth (not shown). The surface 32 is designed to receive adhesive material for bonding the bracket 20 to the tooth.

The distal and mesial tie-wings 28 and 30 comprise a pair of generally vertically oriented, spaced-apart elements. The tie-wings 28 and 30 enable elastics or other force transmitting members or ligatures (not shown) to be connected to the bracket 20. The elastics or ligatures can be connected to either or both of the tie-wings 28 and 30. The upper and lower ends of the tie-wings 28 and 30 are curved toward the base portion 22, forming recesses 34 for retaining the elastics or ligatures.

An arch wire slot 36 is formed near the middle of each of the tie-wings 28 and 30. The arch wire slot 36 is designed to receive an orthodontic arch wire (not shown). The entrances to the slots 36 are chamfered at 38 to allow easy insertion of the arch wire.

Extension members 24 and 26 project distally and mesially, respectively from the bracket 20. The extension members 24 and 26 are engagable with the arch wire to inhibit rotation of the bracket 20 during tooth movement.

A hook member 40 extends gingivally from the mesial tie-wing 30 for facilitating connection of additional elastics, springs or other force transmitting devices (not shown) to the bracket 20. The hook member 40 includes a neck portion 42 and an enlarged ball end portion 44 for securely retaining the force transmitting devices.

The height of the hook member 40, including the ball portion 44, is preferably between 1 and 1.5 mm. It has been found that this height is sufficient for enabling easy attachment of force transmitting devices. Hook members on conventional brackets typically have heights of about 2 mm. One problem encountered with the relatively longer conventional hooks is that force transmitting devices attached to these hooks tend to migrate away from the brackets. As a result, the devices apply force to the brackets at a distance substantially away from the center of the brackets, thereby increasing moments and causing undesirable tipping of the teeth.

The width of the bracket 20 or the distance between the outer ends of the extension members 24 and 26 is preferably the same as that of a conventional single wing bracket.

The bracket 20 may comprise a variety of materials including, for example, stainless steel, ceramics, and plastics.

Figure 5:
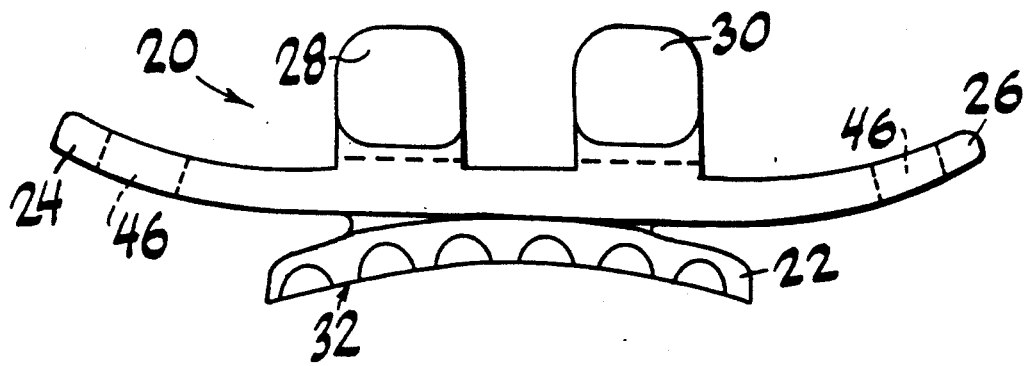
FIG. 5 is a bottom view of a bracket having bent extension members in accordance with the invention.

The extension members 24 and 26 each include a hole 46 extending therethrough to facilitate bending of the members 24 and 26. The extension members 24 and 26 may be bent as shown, for example, in FIG. 5 to vary the degree of contact between an arch wire (not shown) and the bracket 20. A practitioner can thus vary the degree of rotational control provided by the bracket.

Figure 6:
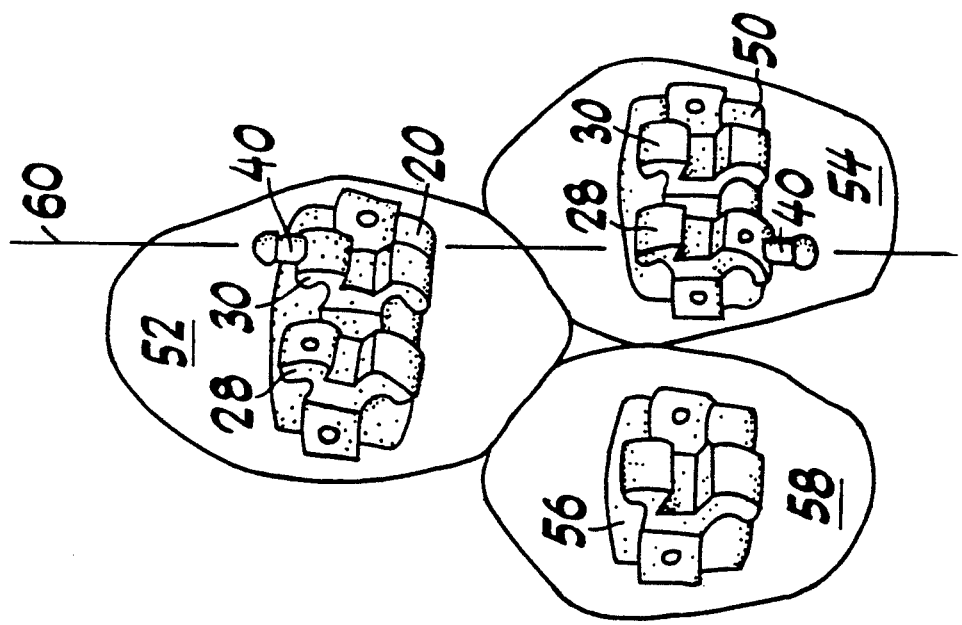
FIG. 6 is an illustration of the placement of brackets on maxillary and mandibular cuspids for providing generally vertical elastic forces.

FIG. 6 illustrates the placement of brackets on upper and lower teeth to provide generally true vertical force elastics in accordance with the invention. Shown in the figure are brackets 20 and 50 affixed to maxillary and mandibular cuspids 52 and 54, respectively. Also shown in the figure is another bracket 56 mounted on an adjacent mandibular tooth 58. The bracket 50 for the mandibular cuspid 54 is similar to the bracket 20 for the maxillary cuspid 52. However, the hook member 40 on the bracket 50 extends gingivally from a distal tie-wing 28 rather than a mesial tie-wing 30 as in bracket 20. With this arrangement of brackets 20 and 50, the hook members 40 can be positioned to be aligned with a generally vertical line 60. Thus, a spring or other force transmitting device (not shown) can be attached to the hook members 40 to apply force to the teeth in a generally vertical direction.

While the brackets 20 and 50 shown are particularly suitable for use on cuspids, it should be noted that they may be used on other teeth.

Figure 7:
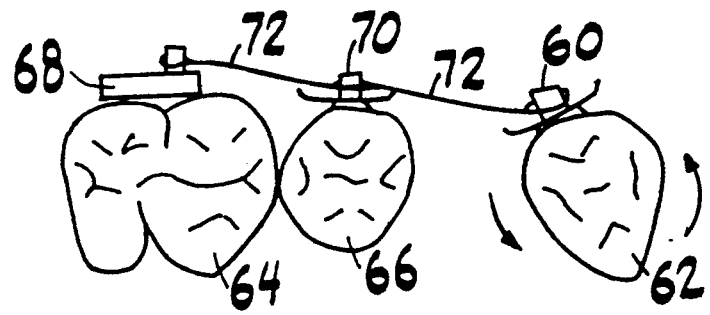
FIG. 7 is an illustration of the rotational tendency of a cuspid during tooth movement using a conventional bracket.
Figure 8:
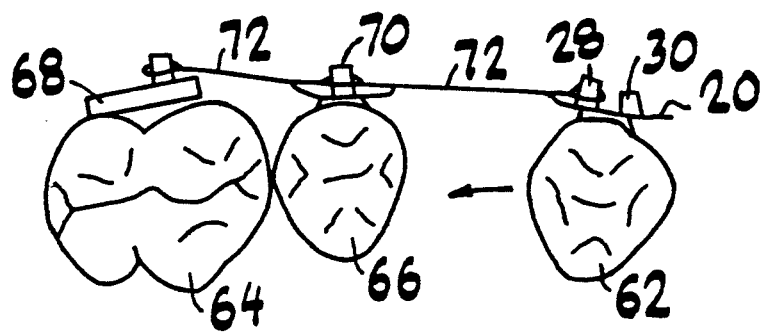
FIG. 8 is an illustration of the improved rotation control provided by a bracket in accordance with the invention.

FIGS. 7 and 8 illustrate additional rotation control provided by brackets in accordance with the present invention. In FIG. 7, a conventional single wing bracket 60 is mounted on a tooth 62, which is being retracted toward teeth 64 and 66. Brackets 68 and 70 are mounted on teeth 64 and 66, respectively. An elastic chain 72 is secured to brackets 60, 68 and 70 to apply force to the tooth 62. Since the bracket 60 on the tooth 62 is a conventional single wing bracket, the elastic chain 72 can only be secured to the bracket near the center of the tooth's labial surface. As a result, force from the elastic chain 72 is applied near the center of the tooth's labial surface, creating substantial moments and causing undesirable disto-lingual rotation of the tooth 62 as shown.

In FIG. 8, a bracket 20 in accordance with the present invention is mounted on the tooth 62 to be retracted. An elastic chain 72 secured to brackets 68 and 70 on teeth 64 and 66, respectively is attached to the distal tie wing 28 of the bracket 20. Securing the chain 72 to the distal tie-wing 28 enables force to be applied to a point distal to the center of the tooth's labial surface. As a result, moments created by the force are reduced as is disto-lingual rotation of the tooth 62. The tooth 62 thus moves toward the teeth 64 and 66 without substantial rotation.

Although the present invention has been described with respect to specific embodiments, various changes and modifications may be suggested to one skilled in the art, and it is intended that the present invention encompasses such changes and modifications as fall within the scope of the appended claims.

What is claimed is:

1. An orthodontic bracket for use with an arch wire to apply corrective forces on a tooth, comprising:
   a pair of spaced-apart, generally vertically oriented tie-wings for attachment of a force transmitting member or a fastening member to either or both said tie wings, each said tie wing including a slot therein for receiving the arch wire; and
   a pair of extension members engagable with the arch wire to control rotation of the tooth, one said extension member projecting mesially from the bracket and the other said extension member projecting distally from the bracket.

2. The orthodontic bracket of claim 1, wherein said extension members are bendable for varying the degree of contact between said extension members and the arch wire.

3. The orthodontic bracket of claim 1, further comprising a hook member for facilitating the connection of a force transmitting device.

4. The orthodontic bracelet of claim 3, wherein said hook member includes an enlarged end.

5. The orthodontic bracket of claim 3, wherein said hook member has a height between 1 to 1.5 mm.

6. The orthodontic bracket of claim 3, wherein said hook member extends gingivally from one of said tie-wings.

7. The orthodontic bracket of claim 1, wherein each of said extension members includes a hole extending therethrough.

8. An orthodontic bracket for use with an arch wire to apply corrective forces on a tooth, comprising:
mesial and distal tie-wings for attachment of a force transmitting member or a fastening member, said tie-wings being generally vertically oriented and spaced apart with each of said tie-wings having a slot therein for receiving the arch wire; and
mesial and distal extension members engagable with the arch wire for rotational control of the tooth, said mesial extension member extending mesially from said mesial tie-wing and said distal extension member extending distally from said distal tie-wing.

9. The orthodontic bracket of claim 8, further comprising a hook member extending gingivally from one of said tie-wings for facilitating connection of a force transmitting device to the bracket.

10. The orthodontic bracket of claim 9, wherein said hook member includes an enlarged ball portion.

11. The orthodontic bracket of claim 9, wherein said hook member has a height between 1 and 1.5 mm.

12. The orthodontic bracket of claim 8, wherein said extension members are bendable for varying the degree of engagement between said extension members and the arch wire.

13. An orthodontic bracket for use in corrective orthodontic treatment of a tooth, comprising
mesial and distal elements for attachment of ligatures or force transmitting members to the bracket, said elements being generally vertically oriented and spaced apart with each of said elements having a slot therein for receiving an arch wire; and
mesial and distal extension members projecting mesially and distally, respectively from the bracket, said extension members being engagable with the arch wire to inhibit rotation of the tooth during the orthodontic treatment.

14. The orthodontic bracket of claim 13, wherein said extension members are bendable for varying the degree of contact between said extension members and the arch wire.

15. The orthodontic bracket of claim 13, further comprising a hook member extending gingivally from one of said elements for facilitating the connection of a force transmitting device.

16. The orthodontic bracket of claim 15, wherein said hook member includes an enlarged ball end.

17. The orthodontic bracket of claim 15, wherein said hook member has a height between 1 and 1.5 mm.

18. An orthodontic bracket for use with an arch wire and an elastomeric chain for orthodontic treatment of a tooth, comprising:
a base portion including a tooth abutting surface;
mesial and distal extension members projecting mesially and distally, respectively from said base portion, said extension members being engagable with the arch wire for inhibiting rotation of the tooth; and
mesial and distal elements joined with said base portion for attachment of the elastomeric chain, said elements being spaced apart so that the elastomeric chain can be connected to either or both to said elements, each of said elements having a slot therein for receiving the arch wire.

19. The orthodontic bracket of claim 18, further comprising a hook member extending gingivally from one of said elements.

20. The orthodontic bracket of claim 19, wherein said hook member includes a neck portion and an enlarged end portion.

21. The orthodontic bracket of claim 19, wherein said hook member is between 1 to 1.5 mm long.

* * * * *